United States Patent [19]

Mitra et al.

[11] Patent Number: 4,791,045
[45] Date of Patent: Dec. 13, 1988

[54] PHOTOSENSITIZERS AND POLYMERIZABLE COMPOSITIONS WITH MANNICH BASES AND IODONIUM SALTS

[75] Inventors: Smarajit Mitra, Woodbury; Robert J. DeVoe, St. Paul, both of Minn.

[73] Assignee: Minnesota Mining and Manufacturing Company, St. Paul, Minn.

[21] Appl. No.: 147,446

[22] Filed: Jan. 25, 1988

[51] Int. Cl.$^4$ .............................................. G03C 1/68
[52] U.S. Cl. ................................ 430/281; 430/919; 430/920; 522/14; 522/15; 522/25
[58] Field of Search .................. 430/281, 919; 522/15, 522/25, 14

[56] References Cited

U.S. PATENT DOCUMENTS

| | | | |
|---|---|---|---|
| 3,458,311 | 7/1969 | Alles et al. | 96/35.1 |
| 4,072,257 | 2/1978 | Fan | 96/87 R |
| 4,072,528 | 2/1978 | Bratt | 96/87 R |
| 4,315,807 | 2/1982 | Felder et al. | 522/33 |
| 4,351,708 | 9/1982 | Berner et al. | 522/15 |
| 4,451,551 | 5/1984 | Kataoka et al. | 430/270 |
| 4,518,676 | 5/1985 | Irving | 430/280 |
| 4,576,975 | 3/1986 | Reilly | 522/13 |
| 4,608,333 | 8/1988 | Ohbayash et al. | 430/281 |

FOREIGN PATENT DOCUMENTS 52-102735 3/1979 Japan.

OTHER PUBLICATIONS

"Photoactive Catalyst Used in Light Induced Photocuring of Coating Systems," Vincent D. McGinniss, Photographic Science and Engineering, vol. 10, No. 3, May/Jun. 1979.

Primary Examiner—Paul R. Michl
Assistant Examiner—Susan E. Shaw McBee
Attorney, Agent, or Firm—Donald M. Sell; Mark A. Litman

[57] ABSTRACT

This invention describes the use of some Mannich bases as photosensitizers for iodonium salts for use in the initiation of free radical polymerization of vinyl monomers. These Mannich bases are unexpectedly more efficient as photosensitizers than are the conventional photosensitizers.

13 Claims, No Drawings

PHOTOSENSITIZERS AND POLYMERIZABLE COMPOSITIONS WITH MANNICH BASES AND IODONIUM SALTS

BACKGROUND OF THE INVENTION

Photosensitizers and photoinitiators, used for the photoinduced free radical polymerization of monomers, are important in radiation curable coatings, bulk polymerization, and the graphic arts. Any improved efficiency in the utilization of incident light to photoinitiate polymerization allows for shorter exposure times or lower light intensities in the photocuring process, whether on a web, in solution or in graphic arts applications.

Carbonyl containing polymeric quaternary ammonium salts as photoinitiators of polymerization have been reported by Shibanov and Protsyuk [Russian Patent USSR No. 787,416, see Chemical Abstracts, 94, 122299r, 1981)]. Photoinitiated polymerization of methyl methacrylate with poly(methylisopropenyl ketone) was taught by Naito et al. [Kobunshi Ronbunshu 36, 777 (1979)]. Carlini et al. [Polymer, 24, 599 (1983)] cured acrylic compositions with benzophenone/dimethylaniline-substituted polymers.

The use of certain photosensitizers with onium salts for initiation of polymerization of ethylenically-unsaturated monomers is also well known in the art. This technique has found applications in printing, duplication, copying, and other imaging systems (see J. Kosar in Light Sensitive Systems: Chemistry and Application of Nonsilver Halide Photographic Procsses, Wiley, New York, 1965, pp 158-193). Aryliodonium salts have been previously described for use as photoinitiators in addition-polymerizable compositions. (See U.S. Pat. Nos. 3,729,313, 3,741,769, 3,808,006, 4,026, 705, 4,069,054, 4,250,053, 4,394,403 and 4,394,403; H. J. Timpe and H. Baumann, *Wiss Z. Tech. Hochsch. Leuna-Merseburg*, 26, 439 (1984); H. Baumann, B. Strehmel, H. J. Timpe and U. Lammel, *J. Prakt. Chem.*, 326 (3), 415 (1984); and H. Baumann, U. Oertel and H. J. Timpe, *Euro. Polym. J.*, 22 (4), 313 (Apr. 3, 1986).

Some monomeric Mannich bases used as free radical photoinitiators has been described in laid open Japanese patent application JA54-37182.

Whereas monomeric and Mannich bases derived from ketones are known, their use as photosensitizers as taught in this invention is novel.

Thus, what the background art has not taught but what this invention teaches is the general use of Mannich base monomers as photosensitizers for iodonium salts for use in the initiation of free radical polymerization of vinyl monomers. Moreover, these Mannich bases are unexpectedly more efficient as photosensitizers than are the conventional photosensitizers.

SUMMARY OF THE INVENTION

It is an aspect of this invention to teach the initiation of polymerization of vinyl monomers in the presence of iodonium salts sensitized by Mannich bases. It is still another object of this invention to indicate the coating of substrates and overcoating of coated substrates with mixtures of a combination of vinyl monomers, iodonium salts, and Mannich bases such that exposure of these mixtures to actinic radiation provides for the resultant polymerization of the vinyl monomers. The compositions of this invention are useful in the field of graphic arts and protective coatings.

DETAILED DESCRIPTION OF THE INVENTION

This invention describes the use of Mannich bases as efficient photosensitizers for onium salt initiation of free radical polymerization. Furthermore, the Mannich bases of this invention are over three times as efficient as is Michler's ketone in the sensitization of iodonium salt initiation of acrylate free radical polymerization; see U.S. Pat. No. 4,228,232. Efficiency refers to the ability to utilize incident light to photoinitiate polymerization. Improved efficiency in the utilization of incident light to photoinitiate polymerization provides for shorter exposure times or lower light intensities or both in the photocuring process, whether on a web, in solution, neat, or in graphic arts applications.

Mannich base photosensitizers of this invention are represented by general formulae I, II and III below.

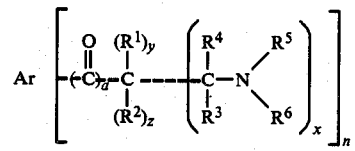

where a=1,2, n=1, 2, 3, 4, x=1, 2, y and z chosen such that x+y+z=3

$R^1$, $R^2$, $R^3$ and $R^4$ may be hydrogen, alkyl, aryl, aralkyl, or alkaryl, $R^5$ and $R^6$ are either independently substituted or unsubstituted alkyl, aryl, alkaryl or aralkyl groups, optionally containing up to 10 heteroatoms, or $R^5$ and $R^6$ together with the nitrogen atom to which they are attached from a heterocyclic group, and Ar is an unsubstituted or substituted aromatic or heteroaromatic organic group.

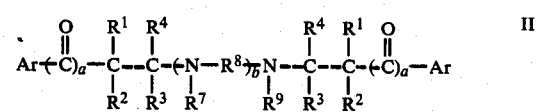

a, $R^1$, $R^2$, $R^3$, $R^4$ and Ar are as defined above; b=0 or 1, $R^7$ and $R^9$ are either independently alkyl, aryl, alkaryl, aralkyl groups, or, $R^7$, $R^9$ together with $R^8$ together with the nitrogens to which $R^8$ is attached selected from the group consisting of heterocyclic groups and bis-heterocyclic groups, forms a divalent organic group, or $R^8$, can be a chemical bond.

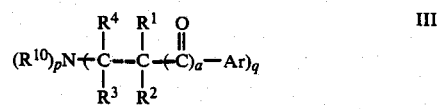

where a, $R^1$, $R^2$, $R^3$, $R^4$ and Ar are as defined above and q=1, 2 or 3, with the proviso that p+q=3, and $R^{10}$ is selected from the group consisting of alkyl, aryl, aralkyl, and alkaryl.

There are preferred ranges and groups for each of the chemical moieties described in formulae I, II and III. $R^1$ and $R^2$ are preferably selected independently from H, aryl, lower alkyl group (1 to 4 carbon atoms), and aralkyl of lower alkyl (1 to 4 carbon atoms) bridging moiety with phenyl, naphthyl, anthryl and phenanthryl aryl groups. $R^3$ and $R^4$ are independently selected from H, alkyl group of 1 to 20 carbon atoms (preferably lower alkyl of 1 to 4 carbon atoms), phenyl group, biphenyl group, aralkyl of lower alkyl bridging moieties (1 to 4 carbon atoms) with phenyl, naphthyl, anthryl, and phenanthryl aryl groups. $R^5$, $R^6$, $R^7$, $R^9$ and $R^{10}$ are preferably independently selected from alkyl of 1 to 20 carbon atoms, aryl of one to three fused aromatic rings (e.g., furanyl, phenyl, naphthyl, anthryl, phenanthryl), and aralkyl having 1 to 20 (preferably 1 to 4) carbon atoms in the alkyl moiety and again phenyl, naphthyl, anthryl, and phenanthryl aryl groups. $R^5$ and $R^6$ may also form, with the nitrogen to which they are attached, a 5- or 6-membered heterocyclic group such as pyrrolidino, piperidino, morpholino, and N-methylpiperazino. $R^7$ and $R^9$ may also form, with the included group $R^8$ and the nitrogen atom to which they are attached, 5- or 6-membered bivalent heterocyclic groups such as piperazine, bis-piperidine (including bis-piperidino alkylenes), and bis-pyrrolidine (including bis-pyrrolidino alkylenes). $R^8$ may preferably be alkylene of 1 to 20 carbon atoms or polyalkylene oxides with up to 40 backbone atoms, or a chemical bond.

The term group can also mean radical, for example an organic group or organic radical and the term heteroaromatic group means any aromatic radical containing one or more hetero atoms which may be the same or different and the term backbone means the main polymer chain.

Mannich bases of this invention represented by general formula I are prepared by the cocondensation of an organic ketone of the general formula IV

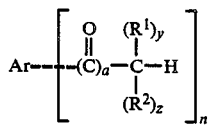

IV where Ar, $R^1$, $R^2$, a, n, y and z are as defined above, with nx equivalents of an organic carbonyl compound having the formula $R^3$—CO—$R^4$ and nx equivalents of an organic amine having the formula $R^5$—NH—$R^6$ where n, x $R^3$, $R^4$, $R^5$ and $R^6$ are as defined above and nx is the arithmatic product of n and x.

Organic ketones of the formula IV which may be used are acetophenone, bromo- or chloro-substituted acetophenones, methyl-substituted acetophenones, methoxy-substituted acetophenones, propiophenone, chloro- or bromo-substituted propiophenones, methyl- or methoxy-substituted propiophenones, valerophenone, phenyl-substituted acetophenones, benzylphenyl ketone, 1- or 2-acetonaphthone, 9-acetylanthracene, 2-, 3- or 9-acetylphenanthrene, n-butyrophenone, 1-phenyl-1,2-propanedione, acetylpyridines, acetylcoumarins, diacetylbenzenes, diacetylnaphthalenes, diacetylanthracenes, diacetylphenanthrenes, diacetylbiphenyls, triacetylbenzenes, triacetylnaphthalenes. The Ar group in IV may also include other aromatic and heteroaromatic groups such as organometallic aromatics (e.g. acetylferrocene etc.).

Organic carbonyl compounds of the formula $R^3$—O—R—$R^4$, where $R^3$ and $R^4$ are as defined above may be formaldehyde, any other organic aldehyde or an organic ketone. While the preferred carbonyl compound of this invention is formaldehyde, other examples of aldehydes that may be used in this Mannich reaction are acetaldehyde, propionaldehyde, butyraldehyde, 2-ethylbutyraldehyde, 2-methylbutyraldehyde, hexanaldehyde, heptaldehyde, valeraldehyde, isovaleraldehyde, octylaldehyde, nonylaldehyde, dodecylaldehyde, 2-methylundecanal, tetradecylaldehyde, undecylaldehyde and trimethyl acetaldehyde. Aromatic aldehydes useful in this reaction are benzaldehyde, o-, m- and p-anisaldehyde and other substituted aromatic aldehydes, 1- and 2-naphthaldehyde, 9-anthraldehyde, phenylacetaldehyde and diphenylacetaldehyde.

Ketones that may be used as the organic carbonyl compound in the Mannich reaction are acetone, 2-butanone, 2- or 3-pentanone, 2- or 3-hexanone, 2-, 3- or 4-heptanone, benzophenone and substituted acetophenones and benzophenones. Other aromatic ketones are 1- or 2-acetonaphthone, 9-acetyl anthracene, 2-, 3- or 9-acetylphenanthrene, 4-acetylbiphenyl, propiophenone, n-butyrophenone, valerophenone, 2-, 3- or 4-acetylpyridine, 3-acetylcoumarin or substituted derivatives of these ketones.

In certain cases, some aldehydes and/or ketones may exist as their more stable dimers, trimers, complexes and the like and they may be used as such. In other cases, the suitable aldehyde or ketone is generated in situ; for example, formaldehyde from paraformaldehyde and acetaldehyde from paraacetaldehyde.

Preferred amines for preparing compounds of the general formula I are secondary amines such as dimethylamine, dibenzylamine, dibutylamine, dicyclohexylamine, didecylamine, diethylamine, dihexylamine, diisoamylamine, diisobutylamine, diisopropylamine, dioctylamine, dipentylamine, dipropylamine, ethyl methyl amine, isopropyl methyl amine, ethyl propyl amine, n-butyl methyl amine, cyclohexyl methyl amine, cyclohexyl ethyl amine, benzyl methyl amine, N-methyl aniline, benzyl ethyl amine, N-ethyl aniline, N-methyl toluidines, N-n-propyl aniline, N-isobutyl aniline, N-butyl aniline, diethanolamine, diisopropanolamine, N-methylethanolamine, morpholine, piperidine, N-methylpiperazine, diphenylamine, 4-benzylpiperidine, 2-, 3- or 4-methylpiperidines, dimethylpiperidines, 4-hydroxypiperidine etc.

Mannich bases of this invention represented by the general formula II are prepared by the cocondensation of two equivalents of an organic ketone of the general formula IV where n=1 with two equivalents of an organic carbonyl compound of formula $R^3$—CO—$R^4$ and one equivalent of a primary amine of formula $R^9$—$NH_2$ or one equivalent of a secondary diamine of the formula $R^7$—NH—$R^8$—NH—$R^9$.

Organic ketones of the formula IV which may be used for the preparation of the compounds of formula II are acetophenone, bromo- or chloro-substituted acetophenones, methyl-substituted acetophenones, methoxy-substituted acetophenones, propiophenone, chloro-, bromo-, methyl- or methoxy-substituted propiophenones, valerophenone, phenyl-substituted acetophenones, benzyl phenyl ketone, 1- or 2-acetonaphthone, 9-acetylanthracene, 2- , 3- or 9-acetyl phenanthrene, n-btyrophenone, 1-phenyl-1,2-propanedione, acetylpyridines, acetylcoumarins etc.

Primary amines of the formula $R^9$—$NH_2$ that may be used are 1- or 2-adamantanamine, allylamine, amylamine, benzylamine, butylamine, sec-butylamine, tert-butylamine, cyclohexylamine, decylamine, dodecylamine, ethanolamine, ethylamine, heptylamine, hexadecylamine, hexylamine, isopropylamine, methylamine, octylamine, aniline, toluidines, anisidines, bromo- or chloro-substituted anilines, 1- or 2-naphthylamine, aminoanthracenes, aminopyridines, picolines etc.

Secondary diamines of the formula $R^7$—NH—$R^8$—NH—$R^9$ that can be used for the preparation of II may be linear or cyclic structures comprising
N,N'-dibenylethylenediamine,
N,N'-diethyl-2-butene-1,4-diamine,
N,N'-diethylethylenediamine,
N,N'-diethyl-1,3-propanediamine,
N,N'-dimethylethylenediamine,
N,N'-dimethyl-1,6-hexanediamine, piperazine,
4,4'-trimethylenedipiperidine, 4,4'-ethylenedipiperidine and the like.

Mannich bases of this invention represented by formula III can be pepared by the cocodensation of q equivalents of an organic ketone of the formula IV (n=1) with q equivalents of an organic carbonyl compound of formula $R^3$—CO—$R^4$ and one equivalent of an organic amine of the formula $(R^{10})_p NH_{3-p}$ where $R^3$, $R^4$, $R^{10}$, p and q are as defined above.

The amines of the formula $(R^{10})_p NH_{3-p}$ that can be used for the preparation of III are ammonia, any of the primary amines described in the preparation of II above or any of the secondary amines described in the preparation of I above.

Reactions for the preparation of photosensitizing Mannich bases may be carried out by methods well known in the art (F. F. Blicke, Organic Reactions, Volume 1, 303-341).

Photosensitive compositions employing the photosensitizers of this invention are prepared from solutions of optionally, a polymeric binder, 0-500 parts by weight, for example of polystyrene, polyacrylates, polymethacrylates, and the like, a photocrosslinkable multifunctional monomer, 50-950 parts by weight, for example of pentaerythritol tetraacrylate, or other multifunctional acrylates, a photoinitiator such as diaryliodonium salts, particularly dipenyliodonium salts, 1-100 parts by weight, a photosensitizer of this invention, 1-50 parts by weight, and optionally, solvent, 0-900 parts by weight. Suitable solvents include 2-butanone, tetrahydrofuran, acetone, aromatic hydrocarbons, chlorinated hydrocarbons, and solvents previously mentioned. Such photosensitive compositions can be coated or used as prepared with or without deoxygenation by purging with an inert gas, for example, nitrogen or argon. Iodonium salts are preferred and are well known in the literature as represented by U.S. Pat. Nos. 3,729,313; 3,741,769; 3,808,006; 4,250,053 and 4,394,403.

The present invention provides a means for photopolymerizing vinyl monomers in solution or neat. When used for polymerization in solution or neat, it is useful to describe the efficiency or photosensitivity of the composition in terms of the amount of light required to cause the sample to reach the gel point, which is defined as the stage at which a liquid begins to exhibit elastic properties and increased viscosities (see the Dictionary of Science and Technology S. P. Parker, 3rd ed., McGraw-Hill, N.Y., 1984, p. 673). Under conditions where samples of equal optical density are irradiated with the same lamp at the same distance the length of time required to reach the gel point, designated hereinafter as the gel time, is inversely proportional to the efficiency for causing polymerization; efficiency being the ability to utilize incident light to photoinitiate polymerization, in this case, measured by gel time. In this invention, a Blak-Ray® lamp (model XX-15, Ultra-Violet Products, Inc., San Gabriel, Calif.) with two 15 watt BLB General Electric bulbs, 366 nanometers primary wavelength, was used for exposing samples to irradiation at a distance of 11 cm.

Gel times are taken as the exposure time required to prevent a solution from flowing in a 12 mm outside diameter Pyrex test tube when inverted. This point is usually reached concomitantly with a precipitous change in the transmittance of visible light, the solution becoming cloudy and opaque. The gel times vary from 5 seconds to 40 minutes, depending on the optical density, light intensity, distance from the exposure source, and the relative amounts of photoinitiator, monomer, solvent, binder, and deoxygenation. Photosensitizers of this invention have gel times one to one-third those of the commonly used photosensitizer, Michler's ketone.

Photosensitive coating solutions employing these photosensitizers are prepared from solutions of a photocrosslinkable multifunctional monomer, for example pentaerythritol tetraacrylate, or other multifunctional acrylates, a photoinitiator like a diarylidonium salt, and a photosensitizer of this invention. An additional component is desired in some constructions. That component is a polymeric binder, for example polystyrene, polyacrylates, polymethacrylates and the like. Other adjuvants such as filler (glass bubbles, silica), pigments, surfactants, coating aids, and the like may be used.

The present invention provides articles including photosensitive coatings and overcoatings on organic and inorganic substrates to give films, composites, or layered structures. These coatings and overcoatings may be applied by methods known in the art such as bar, knife, reverse roll, knurled roll, or spin coatings, or by dipping, spraying, brushing, curtain coating and the like. Preparation of the coatings and overcoatings of this invention involves several steps.

First, a suitable photosensitive coating solution is coated on a substrate such as a polyvinylidene chloride-primed polyester film, as known in the art, and allowed to dry. Other flexible substrates that can be used are plastics such as primed polyethylene and polypropylene, and metal foils, and rigid substrates such as glass, aluminized metal, and aluminum can be used. A suitable solvent for such solutions is 2-butanone. Other organic solvents that are useful for preparing photosensitive coatings are THF, acetone, aromatic hydrocarbons, chlorinated hydrocarbons, dioxane, and solvents previously mentioned.

Second, the resultant dried photosensitive coating can be optionally overcoated with a poly(vinyl alcohol) coating or other coatings which serve as oxygen barriers. Such techniques are shown in U.S. Pat. Nos. 3,458,316; 4,072,528 and 4,072,527. The poly(vinyl alcohol) overcoating is prepared by coating an aqueous solution of polyvinylalcohol onto a photosensitive layer. The resultant overcoated film or composite is dried and then exposed to radiation of a suitable wavelength for a suitable length of time. Usually 30 seconds is the preferred length of time although the exposure time can be from 1 to 1000 seconds depending on the desired extent of cure.

Any suitable source which emits ultraviolet light may be used to activate the photosensitizers in the practice of this invention. Suitable sources are xenon arcs, carbon arcs, low-, medium-, and high-pressure mercury lamps, plasma arcs, ultraviolet light-emitting diodes and ultraviolet emitting lasers. In this invention, exposure to ultraviolet light of the composite was conducted in a Berkey Ascor exposure unit using two kilowatts (kw) of power. The resultant negative images obtained were developed by rinsing the exposed composite with water for the removal of polyvinyl alcohol followed by rinsings with 2-butanone to remove unexposed photosensitive coating. A comparison of the photographic speed as measured using a 21 step (square root of two) sensitivity guide shows comparable speeds of photosensitive coatings made according to this invention compared to those photosensitive coatings that contained commercially available photoinitiators (for example, Irgacure 651, benzil dimethyl ketal, commercially available from Ciba-Geigy, Ardsley, NY). Furthermore, a comparison of samples of constructions in which either the photosensitive iodonium salt or Mannich base has been left out shows that both materials are essential for providing an effective photosensitive composition. In regard to the sensitivity guide, more steps mean more sensitivity in negative working imaging systems.

Objects and advantages of this invention are further illustrated by the following examples, but the particular materials and amounts thereof recited in these examples, as well as other conditions and details, should not be construed to unduly limit this invention.

EXAMPLES

In the following examples, parts are reported as parts by weight unless indicated otherwise, and polymer structures were confirmed spectroscopically. ;cl EXAMPLE 1

This example describes the preparation of the Mannich base V given by the structure

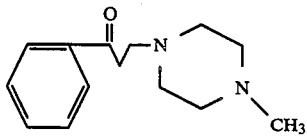

A solution of 250 parts acetophenone, 208 parts N-methylpiperazine, 121 parts paraformaldehyde, 80 parts methanol, and 35 parts concentrated hydrochloric acid were mixed and refluxed under argon 20 hours. 30 parts paraformaldehyde was added and reflux continued for 2 hours more. The solution was placed in a refrigerator overnight to crystallize. The white solid was collected by filtering through a frit, washed with minimal water and methanol, and recrystallized from methanol to yield 314 parts white needles, $^1$H nmr confirmed the structure as V.nHCl, m.p. 194°–195° C. (dec.). The free base was prepared from V.nHCl by dissolving 2 parts of the hydrochloride salt in 75 parts water, adding 10% aqueous sodium hydroxide until basic, and extracting with ether. The ether is dried with anhydrous potassium carbonate, filtered and the ether removed at reduced pressure, leaving the ree base.

EXAMPLE 2

This example describes the synthesis of the Mannich base VI given by the structure

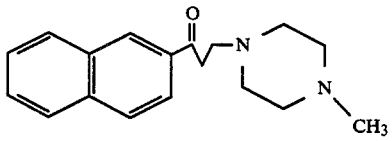

A solution of 1099 parts f N-methylpiperazine, 3766 parts of p-toluenesulfonic acid monohydrate and 450 parts of paraformaldehyde in 3000 parts of methanol was stirred overnight in room temperature. To this was added a solution of 1700 parts of 2-acetonaphthone in 4000 parts of methanol and the resulting mixture was heated to reflux for 16 hours and then cooled to room temperature. The mixture was made basic with 10% NaOH and extracted with ether. The ether layer was extracted with 10% HCl solution, washed with ether and made basic again with 10% NaOH and again extracted with ether. This ether extract was dried with anhydrous potassium carbonate, filtered and the ether removed under reduced pressure. The white crystalline solid obtained was twice recrystallized from hexane to afford a white crystalline solid, m.p. 73°–74° C. Elemental analysis: calcd. 76.6%C, 7.8%H, 9.9%N; found 76.4%C, 7.8%H and 9.9%N. The infrared and NMR spectrum confirmed the structure VI.

EXAMPLE 3

The compound 3-dimethylaminopropiophenone (VII) was prepared from its hydrochloride salt, which is available commercially from Aldrich Chemical Company, Inc., Milwaukee, Wis. The Mannich base hydrochloride was dissolved in water and neutralized with 10% sodium hydroxide solution to liberate the free base which was extracted with diethyl ether. The ether solution was dried with anhydrous potassium carbonate and evaporated to give pure 3-dimethylaminopropiophenone (VII).

EXAMPLE 4

The compound N,N,N',N'-tetramethyl-2-benzoyl-1,3-propanediamine (VIII) was synthesized by the method of Kinast and Tietze, Angew. Chemie. Int. Ed. 15 239–240 (1976). A mixture of 500 parts of N,N-dimethylmethylene ammonium chloride, 2600 parts of dry acetonitrile and 1035 parts of compound VII, described above, was heated to reflux under nitrogen for 15 minutes. The mixture was allowe to cool to room temperature andd then placed in the refrigerator overnight. A total of 800 parts of the hydrochloride salt of VI was isolated by filtration. The mother liquor was made basic with 10% NaOH solution and extracted with ether, the ether solution dried with anhydrous potassium carbonate and the ether evaporated under reduced pressure to yield 479 parts of a light yellow, low melting solid identified as VIII by NMR spectroscopy. The total yield of VIII was thus 93%.

EXAMPLE 5

This example describes the preparation of the Mannich base IX given by the structure

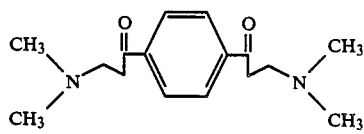

A mixture of 162 parts of p-diacetylbenzene, 241 parts of paraformaldehyde and 167 parts of dimethylamine hydrochloride was dispersed in 800 parts of ethanol and the mixture was refluxed under nitrogen after acidification with 8 parts of conc. HCl. After 18.5 hours of reflux, the ethanol was removed under reduced pressure. The remaining solid was dissolved in hot methanol and recrystallized by the addition of ether. The solids were filtered after cooling, washed with ether and dried under vacuum to give 210 parts of the hydrochloride of IX. A solution of this material in water was basified with 10% NaOH solution and the free base was extracted with ether and the extract was dried with anhydrous sodium carbonate. On evaporation of the ether 138 parts of the compound IX was obtained as an off-white solid (50% yield) which was identified by NMR to be the free base IX.

EXAMPLE 6

This example describes the synthesis of the Mannich base X given by the structure

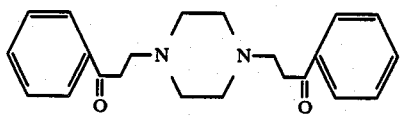

A mixture of 120 parts of acetophenone, 43 parts of anhydrous piperazine, 120 parts of paraformaldehyde and 400 parts of ethanol was treated with enough conc. HCl to bring the pH to 1 and refluxed under a nitrogen blanket for 40 hours. The solvent was removed under reduced pressure and the solid was taken up in water, basified with 10% NaOH and the precipitated solid extracted out with ethyl acetate. The extract was dried with anhydrous sodium carbonate and evaporated to give 105 parts of a solid. The solid was redissolved in 10% HCl, basified with 10% NaOH, extracted with ethyl acetate and the extract was dried with anhydrous sodium carbonate and concentrated under reduced pressure. Sufficient ether was added to precipitate a white crystalline solid, which was filtered, washed with ether and dried under a vacuum. This yielded 88 parts (50%) of the free base X with a melting point of 140°–152° C. [reported to be 141.5°–144° C. by V. Valenta, M. Bartosova and M. Protiva in Coll. Czech. Chem. Comm. 46 1280 (1981)].

EXAMPLE 7

This example provides the synthesis of the Mannich base XI given by the formula

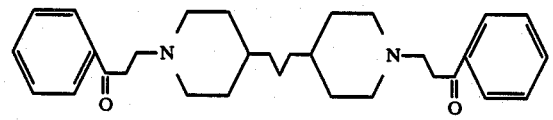

To a mixture of 105 parts of 4,4'-trimethylenedipiperidine and 200 parts of methanol was added 60 parts of glacial acetic acid. After addition was complete, 81 parts of 37% aqueous formalin was added and the clear solution was stirred overnight at room temperature. This solution was added to a solution of 120 parts of acetophenone in 200 parts of N,N-dimethylformamide and the mixture was heated to 70° C. under a nitrogen blanket for 22 hours. The solution was poured into 5000 parts of aqueous NaOH and the gummy precipitate was separated by decantation. This was redispersed in 500 parts of N,N-dimethylformamide and reprecipitated into aqueous NaOH. The solids were separated by filtration, washed with water and dried to give 144 parts of an off-white solid product which was identified by infrared and NMR as the compound XI.

EXAMPLE 8

The following example compares the photosensitizers of this invention with state-of-the-art photosensitizers in solution polymerization of pentaerythritol tetraacrylate.

A stock solution of 5 parts of pentaerythritol tetraacrylate, 44.5 parts of methyl ethyl ketone, and 0.5 parts of diphenyliodonium hexafluorophosphate was prepared. To 3 ml aliquots of the stock solution was added sufficient sensitizer (Table 1) to adjust the absorbance at 366 nm to 0.053±0.002 vs stock solution in a 1 cm. path length cell. After transferring to 12 mm o.d. Pyrex test tubes and deoxygenating by nitrogen purge for 10 minutes, each sample was irradiated using a Blak-Ray® lamp (Model XX-15, Ultra-Violet Products, Inc., San Gabriel, Calif., primary wavelength 366 nm) with 15 watt BLB General Electric Company bulbs at a distance of 11 cm. The time required to cause each sample to gel (no flow, opaque) was recorded and is reported in Table 1. The data show that the Mannich bases of this invention are better sensitizers (shorter gel times) than any of the other photosensitizers, including the standard photosensitizer, Michler's ketone.

TABLE 1

| Photosensitizer No. | Gel time (in seconds) |
---|---
| 1. Michler's ketone | 165 |
| 2. Acetophenone | 510 |
| 3. 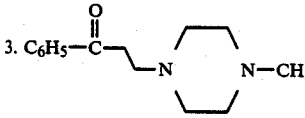 V | 54 |
| 4. 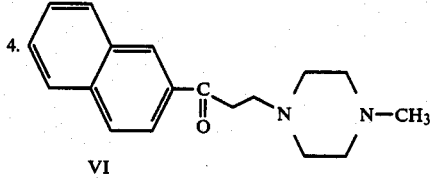 VI | 50 |
| 5. Ph—C(O)—CH₂—NMe₂  VII | 43 |
| 6. (Ph—C(O)—CH—NMe₂)₂  VIII | 45 |
| 7. 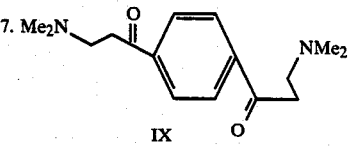 IX | 54 |

TABLE 1-continued

| Photosensitizer No. | Gel time (in seconds) |
|---|---|
| 8. 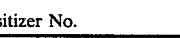 | 130 |

EXAMPLE 9

The following example extends the application of the photosensitizers of this invention to films.

Photosensitive films were prepared by bar coating (#20 wire-wound bar) polyvinylidene chloride-primed polyester film (3M film MF 477400, 3M, St. Paul, MN) using a solution of 0.01 part photosensitizer XI, 0.05 part diphenyliodonium hexafluorophosphate, 0.44 part pentaerythritol tetraacrylate, 0.50 part polystyrene (Aldrich Chemical Co., Milwaukee, Wis., molecular weight 22,000) which serves as a binder, and 4.5 parts methyl ethyl ketone. The coating was dried with a heat gun, then in an oven at 50° C. for two minutes. An oxygen barrier coating of 1 part polyvinyl alcohol (Aldrich Chemical Co., Milwaukee, Wis., molecular weight 2,000, 75% hydrolyzed), 0.02 part 10% aqueous solution of Triton X100 (Rohm and Haas Co., Philadelphia, Pa.), and 20 parts water was applied over the first coating using a #8 wire-wound bar and dried as with the first coating. Exposure was made with UV light in a 2 kw Berkey-Ascor exposure unit with a mercury arc for 30 seconds through a 21 step (square root of two) sensitivity guide. The negative image was developed by rinsing the exposed sample with water for 10 seconds (to remove polyvinyl alcohol topcoat) followed by a methyl ethyl ketone rinse for 15 seconds (to remove the unexposed areas of the coating), leaving 7 steps adhered to the polyester. When either the photosensitizer (Mannich base) of this invention or the iodonium salt were left out of the composition, no image was obtained (0 steps). Substitution of commercial Irgacure 651 (Ciga-Geigy Corp., Ardsley, N.Y.) for the photosensitizer shown above and diphenyliodonium hexafluorophosphate left 11 steps, comparable to the 7 steps from photosensitizers of this invention.

EXAMPLE 10

The purpose of this example is to show that the photosensitizers of this invention fall outside of the specifications of photosensitizers for iodonium salts described in U.S. Pat. Nos. 3,729,313, 3,741,969, and 3,808,006.

A solution of 5 parts 5% weight/volume Butvar B76 (Shawinigan Resins Co., Springfield, Mass.), 0.3 part trimethylolpropane trimethacrylate, 0.03 part 2-methyl-4,6-bis(trichloromethyl)-s-triazine, and 0.01 part photosensitizer number VII of this invention was knife coated on 3 mil polyvinylidene chloride-primed polyester film using a 2 mil orifice. The coating was air-dried for 40 minutes. A second 3 mil polyvinylidene chloride-primed polyester film was placed over the dry, tacky coating. The resultant sandwich construction was then exposed through a #1-T Resolution Guide (Stouffer Graphic Arts Equipment Co., South Bend, Ind.) for 3 minutes to 15,000 foot candles of incident light from a tungsten light source providing light in the visible and ultraviolet range (3M quartz-iodine lamp, #78-8454-3463-4E, 3M, St. Paul, MN). The cover film was removed and the coating was treated with black toner powder (#78-6969-5581-0, 3M, St. Paul, MN), yielding no visible image.

What is claimed is:

1. A photopolymerizable composition comprising a photosensitizationally effective amount of Mannich base photosensitizer compounds of the formulae:

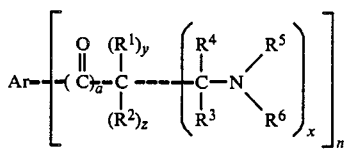

where $a = 1, 2$, $n = 1, 2, 3, 4$, $x = 1, 2$, y and z chosen such that $x + y + z = 3$ $R^1$, $R^2$, $R^3$ and $R^4$ may be hydrogen, alkyl, aryl, aralkyl, or alkaryl, $R^5$ and $R^6$ are either independently substituted or unsubstituted alkyl, aryl, alkaryl or aralkyl groups, optionally containing up to 10 heteroatoms, or $R^5$ and $R^6$ together are selected from the group consisting of carbocyclic and heterocyclic groups, and Ar is an unsubstituted or substituted aromatic or heteroaromatic organic group

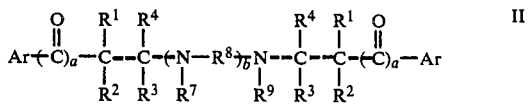

where a, $R^1$, $R^2$, $R^3$, $R^4$ and Ar are as defined above and $b = 0$ or 1, $R^7$ and $R^9$ are either independently alkyl, aryl, alkaryl, aralkyl groups, or, $R^7$ and $R^9$ together with $R^8$ together with the nitrogens to which $R^8$ is attached forms a divalent organic group selected from the group consisting of heterocyclic groups and bis-heterocyclic groups, or $R^8$ is a chemical bond

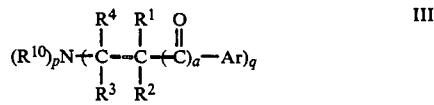

where a, $R^1$, $R^2$, $R^3$, $R^4$ and Ar are as defined above and where $q = 1, 2$ or 3, with the proviso that $p + q = 3$, and $R^{10}$ is selected from the group consisting of alkyl, aryl, aralkyl, and alkaryl said Mannich base photosensitizer being in physical association with a photosensitive free radical diaryliodonium photoinitiator and at least one vinyl monomer.

2. A photopolymerizable composition of claim 1 having a photosensitizer of structural formula (I) wherein $R^1$, $R^2$ are independently selected from the group consisting of H and alkyl groups of 1 to 20 carbon atoms, and $R^3$ and $R^4$ are H.

3. The photopolymerizable composition of claim 1 having a photosensitizer of structural formula (II) wherein $R^1$, $R^2$ and $R^3$ are independently selected from the group consisting of H and alkyl groups of 1 to 20 carbon atoms.

4. The composition of claim 1 having structural formula (I) wherein $R^5$ and $R^6$ are either independently substituted or unsubstituted alkyl, aryl, alkaryl or aralkyl groups, optionally containing up to 10 heteroatoms, or $R^5$ and $R^6$ together with the nitrogen atom to which they are attached from a heterocyclic group, and Ar is an unsubstituted or substituted aromatic or heteroaromatic organic group.

5. The composition of claim 1 having structural formula (II) wherein $R^7$ and $R^9$ are independently selected from alkyl of 1 to 20 carbon atoms, aryl of one to three fused rings, and aralkyl having 1 to 20 carbon atoms in the alkyl moiety thereof and wherein the aryl moiety thereof is selected from phenyl, naphthyl, anthryl and phenanthryl, or wherein $R^7$ and $R^9$ together with atoms from $R^8$ and the nitrogen atoms attached to $R^8$ form 5- or 6-membered heterocyclic groups selected from piperizine, bis-piperidine, and bis-pyrrolidone.

6. The composition of claim 3 wherein $R^7$ and $R^9$ are independently selected from alkyl of 1 to 20 carbon atoms, aryl of one to three fused rings, and aralkyl having 1 to 20 carbon atoms in the alkyl moiety thereof and wherein the aryl moiety thereof is selected from phenyl, naphthyl, anthryl and phenanthryl, or wherein $R^7$ and $R^9$ together with atoms from $R^8$ and the nitrogen atoms attached to $R^8$ form 5- or 6-membered heterocyclic groups selected from piperizine, bis-piperidine, and bis-pyrrolidine.

7. An article comprising the composition of claim 1 coated onto a substrate.

8. An article comprising the composition of claim 2 coated onto a substrate.

9. The article of claim 7 having an oxygen barrier topcoat thereon.

10. The article of claim 8 having an oxygen barrier topcoat thereon.

11. The composition of claim 9 further comprising a polymeric binder.

12. The composition of claim 10 further comprising a polymeric binder.

13. The composition of claim 1 having a photosensitizer of structural formula III wherein $R^1$ and $R^2$ are independently selected from H and alkyl of 1 to 20 carbon atoms and $R^3$ and $R^4$ are H.

* * * * *

UNITED STATES PATENT AND TRADEMARK OFFICE
CERTIFICATE OF CORRECTION

PATENT NO. : 4,791,045
DATED : December 13, 1988
INVENTOR(S) : Mitra and DeVoe

It is certified that error appears in the above-identified patent and that said Letters Patent is hereby corrected as shown below:

Column 3, line 62 "$R^3$-O-R-$R^4$" should be --$R^3$-CO-$R^4$--.

Column 5, line 15 "pepared" should be --prepared--.

Column 7, line 56 "ree" should be --free--.

Column 8, line 1 "f" should be --of--.

Column 8, line 41 "allowe" should be --allowed--.

Column 8, line 42 "andd" should be --and--.

Column 11, line 43 "Ciga" should be --Ciba--.

Column 11, line 53 "3,741,969" should be --3,741,769--.

Column 1, line 34, "Procsses" should read -- Processes --.

Signed and Sealed this

Twenty-first Day of November, 1989

Attest:

JEFFREY M. SAMUELS

Attesting Officer     Acting Commissioner of Patents and Trademarks